US009205605B2

(12) United States Patent
Lee

(10) Patent No.: US 9,205,605 B2
(45) Date of Patent: Dec. 8, 2015

(54) MULTI-FUNCTION DETECTION LINER FOR MANUFACTURING OF COMPOSITES

(75) Inventor: Wei-Yueh Lee, Arlington, TX (US)

(73) Assignee: Textron Innovations Inc., Providence, RI (US)

( * ) Notice: Subject to any disclaimer, the term of this patent is extended or adjusted under 35 U.S.C. 154(b) by 535 days.

(21) Appl. No.: 13/455,855

(22) Filed: Apr. 25, 2012

(65) Prior Publication Data

US 2013/0283920 A1    Oct. 31, 2013

(51) Int. Cl.
| | |
|---|---|
| G01N 29/00 | (2006.01) |
| B32B 41/00 | (2006.01) |
| B32B 38/10 | (2006.01) |
| B32B 37/14 | (2006.01) |
| B29C 70/54 | (2006.01) |
| B29C 33/68 | (2006.01) |
| G01N 27/90 | (2006.01) |
| G01N 29/04 | (2006.01) |

(52) U.S. Cl.
CPC .............. *B29C 70/54* (2013.01); *B29C 33/68* (2013.01); *G01N 27/90* (2013.01); *G01N 29/04* (2013.01)

(58) Field of Classification Search
CPC ........ B29C 70/54; B29C 33/68; G01N 29/04; G01N 27/90
USPC .................... 73/649; 156/64, 247; 428/40.1
See application file for complete search history.

(56) References Cited

U.S. PATENT DOCUMENTS

| | | | | |
|---|---|---|---|---|
| 4,685,987 | A | * | 8/1987 | Fick ............................. 156/247 |
| 5,073,595 | A | * | 12/1991 | Almer et al. .................... 525/65 |
| 6,551,247 | B2 | * | 4/2003 | Saito et al. ..................... 600/459 |
| 6,716,529 | B2 | * | 4/2004 | Sawamura et al. ........... 428/413 |
| 7,468,199 | B2 | * | 12/2008 | Divigalpitiya et al. ...... 428/40.1 |
| 7,744,991 | B2 | | 6/2010 | Fischer et al. |
| 8,377,535 | B2 | * | 2/2013 | Nakagawa et al. .......... 428/41.8 |
| 8,709,188 | B2 | * | 4/2014 | Rocker et al. ................. 156/189 |
| 2002/0182955 | A1 | | 12/2002 | Weglewski et al. |
| 2003/0037512 | A1 | | 2/2003 | Finestone et al. |
| 2003/0129343 | A1 | | 7/2003 | Galkiewicz et al. |
| 2006/0108056 | A1 | | 5/2006 | Sarr |

(Continued)

FOREIGN PATENT DOCUMENTS

JP          2006215024          *  8/2006

OTHER PUBLICATIONS

Extended European Search Report in related European patent application 12174243, mailed Oct. 30, 2013, 5 pages.

(Continued)

*Primary Examiner* — J M Saint Surin
(74) *Attorney, Agent, or Firm* — James E. Walton; Brian E. Harris

(57) ABSTRACT

A multi-function detection liner is applied to a non-cured composite material at the point of manufacturing for building a composite part. The detection liner includes a first insulative layer and a first conductive layer. The detection liner is configured to be detectable from a plurality of non-destructive inspection tests. The first insulative layer is detectable by ultrasound and radiograph within the composite part. The first conductive layer is configured to provide an eddy current signal and to enhance ultrasound attenuation of the detection liner within the composite part. Alternatively, the detection liner may include an integrated layer that combines the functions of an insulative layer and a conductive layer. The detection liner is releasably bonded to a surface of the non-cured composite material.

11 Claims, 6 Drawing Sheets

(56) References Cited

U.S. PATENT DOCUMENTS

| | | |
|---|---|---|
| 2007/0166523 A1 | 7/2007 | Fukaya |
| 2007/0212551 A1* | 9/2007 | Collins ............... 428/414 |
| 2007/0259027 A1 | 11/2007 | Miller, II et al. |
| 2011/0073357 A1* | 3/2011 | Zenz ................. 174/257 |
| 2012/0012382 A1 | 1/2012 | McBain |
| 2012/0111622 A1* | 5/2012 | Daigaku et al. ........... 174/259 |

OTHER PUBLICATIONS

Office Action dated May 6, 2014 from counterpart CA App. No. 2805949.

* cited by examiner

| Layer | Layer Type | Sample Layer Form | 101 | 201 | 301 | 401 | 501 | 601 | 701 | 801 |
|---|---|---|---|---|---|---|---|---|---|---|
| 1 | Release Coating | Silicon-A | x | x | x | x | x | x | x | Combined/Integrated |
| 2 | Insulator | Paper, plastic, fabric | x | x | x | x | x | x | Combined/Integrated | |
| 3 | Conductor | Flakes, strips, wires, mesh, foil | x | x | x | Combined/Integrated | x | Combined/Integrated | | |
| 4 | Insulator | Paper, plastic, fabric | | x | x | | x | Combined/Integrated | | |
| 5 | Conductor | Flakes, strips, wires, mesh, foil | | | x | | x | x | | |
| 6 | Insulator | Paper, plastic, fabric | | | | | x | | | |
| 7 | Release Coating | Silicon-B | Opt. | Opt. | Opt. | Opt. | Opt. | Opt. | Opt. | Opt. |

FIG. 2

MULTI-FUNCTION DETECTION LINER FOR MANUFACTURING OF COMPOSITES

BACKGROUND

1. Field of the Invention

The present application relates generally to the manufacturing of composite materials and composite parts and, more particularly, to a multi-function detection liner applied to the composite material.

2. Description of Related Art

High performance fiber reinforced composite materials such as those used in space and aerospace applications are manufactured by impregnating dry fibrous material forms, such as unidirectional fibers or woven fabrics, with uncured resins. A resin impregnated fibrous material is also called a prepreg material or a prepreg. A composite part may be laid-up or formed using an automated fiber material placement process, but may also be laid-up by hand. The process includes layering isolated layers of prepreg material to build composite parts of assorted shapes and sizes. This process permits the construction of almost limitless different shaped and sized parts.

Conventional prepreg manufacturing typically involves one of several different resin impregnation processes. A resin can be applied to a conventional paper liner and transferred to the dry fibrous material or applied directly to the dry fibrous material. The resin is impregnated within the dry fibrous material by applying a heating process to melt and infuse the resin. The heating process may include temperatures of around 200 degrees Fahrenheit or more. Prior to shipping, a portion of the conventional liner is removed. In either situation above, the manufacturing of a laid-up composite part generally includes the application of a conventional paper liner to one or more sides of the prepreg material capable of withstanding the resin infusion pressure at elevated temperatures.

The conventional liner has many disadvantages. A paper liner is often used in prepreg manufacturing processes because paper, when properly selected or engineered, can withstand the heat and pressure exerted by resin impregnation and consolidation, and it often costs less than other material alternatives. However, conventional paper liners have disadvantages. When unintentionally left on a prepreg during layup of the part, the paper liner cannot easily be detected by typical production non-destructive inspection methods, such as Eddy-current, ultrasound, and radiograph. Retention of any portion of the liner between layers can have negative implications. If a liner is found within a composite part, the material would typically need to be reworked or scrapped, thereby resulting negatively in any delivery schedules. Additionally, the composite part could be weakened at the location of the residual liner which may lead to failure of the part while in use.

Due to this disadvantage, paper liners on the prepreg, as received from the material supplier, are typically removed and replaced with two metalized plastic liners, one on each side of the prepreg. These metalized plastic liners are generally detectable by Eddy-current methods but can be difficult to be detected by ultrasound methods, and may not be detected by the radiograph method. It is possible that liners, even though detectable by one method, may not be detected for various reasons, for example, liner size, process protocol, and others. Therefore, it is important that a liner, if embedded in a cured part, can be detected by a plurality of different production non-destructive inspection methods. Replacing paper liners with the metalized plastic liners consists of approximately 40 percent of the total time spent in converting prepreg from an as-received good to finished cut plies ready for layup.

Another disadvantage of conventional liners includes a relative susceptibility to tearing due to a lack of strength in the liner and an inability to withstand the heating process to infuse the resin within the dry fibrous material. A stronger and more detectable liner is needed. A liner capable of meeting the functions of the traditional liner while also being detected by typical production non-destructive inspection methods at various stages of a part manufacturing processes is desired.

Although great strides have been made in liners for prepreg materials, considerable shortcomings remain.

DESCRIPTION OF THE DRAWINGS

The novel features believed characteristic of the application are set forth in the appended claims. However, the application itself, as well as a preferred mode of use, and further objectives and advantages thereof, will best be understood by reference to the following detailed description when read in conjunction with the accompanying drawings, wherein:

FIG. 2 is a table illustrating features and characteristics of selected embodiments of the multi-function liner according to the present application;

Figure 1:
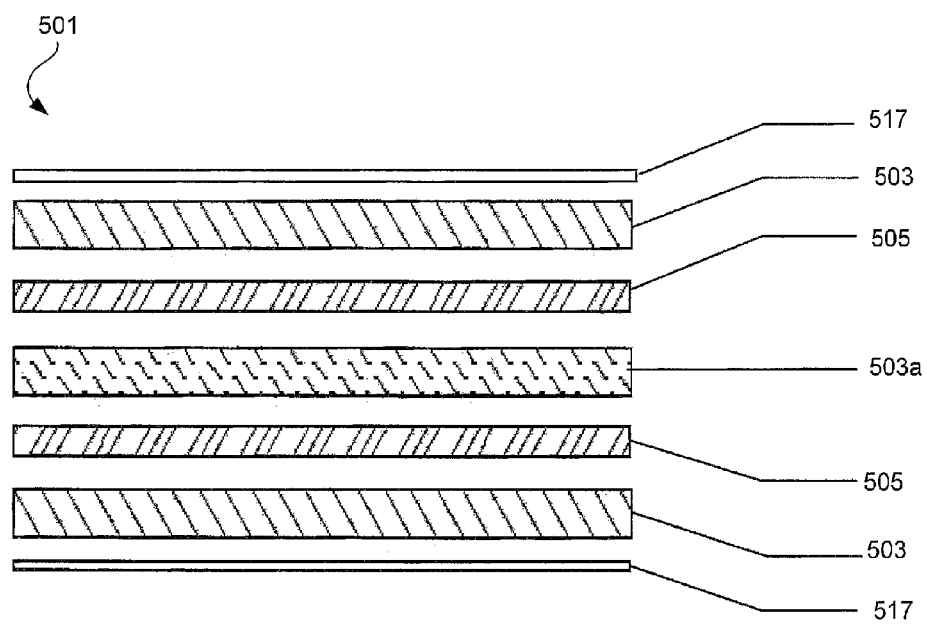
FIG. 1 is an enlarged side view of a single embodiment of a multi-function liner according to the present application having multiple insulative and conductive layers.

While the system and method of the present application is susceptible to various modifications and alternative forms, specific embodiments thereof have been shown by way of example in the drawings and are herein described in detail. It should be understood, however, that the description herein of specific embodiments is not intended to limit the application to the particular embodiment disclosed, but on the contrary, the intention is to cover all modifications, equivalents, and alternatives falling within the spirit and scope of the process of the present application as defined by the appended claims.

DETAILED DESCRIPTION OF THE PREFERRED EMBODIMENT

Illustrative embodiments of the preferred embodiment are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms to describe a spatial relationship between various components or to describe the spatial orientation of aspects of such components should be understood to describe a relative relationship between the components or a spatial orientation of aspects of such components, respectively, as the device described herein may be oriented in any desired direction.

Referring now to FIG. 1 in the drawings, a multi-function liner 501 is illustrated. Multi-function detection liner 501 is one embodiment of a multi-function liner according to the present application. A description of the embodiments is found below. A multi-function liner is configured to have one or more layers that allow it the capability of protecting and sealing a prepreg material while also being detected by a plurality of typical production non-destructive inspection methods at various stages of the composite part manufacturing processes. As such, the multi-function liner includes at least one of a conductive layer 505 and an insulative layer 503, 503a. Liner 501 also illustrates use of a silicone layer 517. The multi-function liner is a combination of multiple materials mixed and consolidated by either mechanical or chemical means. The multi-function liner is optimized in its material constituents, in the layers laminating order, and in the binding material, so as to meet the liner functional requirements throughout the composite part manufacturing process, including but not limited to, spatial dimensions, flexibility, flatness, mechanical strength, porosity, electrical conductivity, and capacitance to name a few. Although illustrated and described as having discrete and/or separate conductive and insulative layers, it is understood that some alternative embodiments combine and/or integrate the properties of conducting and insulative layers into a single layer.

Referring now also to FIG. 2 in the drawings, a table 90 is illustrated that depicts a selection of the various embodiments 95 of the multi-function liner. Liner 501 is depicted in FIG. 1 to illustrate multiple conductive and insulative layers 503, 505 and serves as a singular embodiment of the multi-function liner. Where multiple layers of each type are used, the layers 91 alternate between types 93: conductive and insulative, as seen with liner 501.

Each embodiment of the multi-function liner bonds together individual insulative layers to conductive layers. The bonding of insulative layers and conductive layers can be done by an adhesive. The adhesive layer may be water based or a solvent based pressure sensitive adhesive. Water based adhesive can tend to bubble when subjected to certain levels of increased temperatures. Therefore, it is preferred that a solvent based adhesive is used with the multi-function liner.

The multi-function liner is configured to provide a number of functions. For example, the multi-function liner is configured to releasably couple to a surface of prepreg material 107 (see FIGS. 3 and 4), such as a non-cured composite material or prepreg, so as to protect material 107 from drying out and from sticking prematurely to other objects. Furthermore, the multi-function liner is also configured to be detectable to a plurality of non-destruction inspection tests. Although the multi-function liner is being described with material 107, it is understood that the multi-function liner is not so limited may be used with other materials. For purposes in this application, material 107 will be prepreg material.

Prepreg tends to have a tacky surface which allows the multi-function liner to couple to a surface of material 107 adhesive-free, meaning without the need of additional adhesives. However, a releasable adhesive may be used to secure layer 93 to the surface of material 107 if material 107 is not prepreg. It is to be understood that some methods of forming material 107 include use of the multi-function liner in providing the resin to be infused, therefore both the multi-function liner and material 107 form a composite assembly used to build composite parts.

Non-destructive inspection tests used to inspect for defects in composite parts during and after the lay-up process are: eddy-current tests, ultrasound tests, and radiograph tests. Eddy-current tests may be performed before and after curing of a composite part to isolate defects. Ultrasound and radiograph tests are performed after curing of the composite part to isolate defects. Eddy-current tests operate with conductive materials and can facilitate detection through ultrasound and radiograph tests. One advantage of ultrasound and radiograph testing is the ability to test the entire part more easily than with Eddy-current test which are performed by hand. The multi-function liner of the present application combines the attributes of conductive and insulative materials to form a single liner capable of detection through a plurality of non-destructive inspection tests. Such multi-function liner is configured to be applied to a non-cured composite material, or to help form a non-cured composite material, at the point of manufacturing to meet the liner functional requirements throughout the entire composite part manufacturing process.

A conductive layer is formed from a predominantly conductive material. A conductor can be metal of any form 97 including, but not limited to, powder, flakes, solid or braided wires, strips, wire mesh, and foil to name a few. The conductivity of a conductive layer is selected and configured to provide adequate eddy current signals and, whenever feasible, to enhance ultrasound reflection properties for detection by a plurality of non-destructive inspection tests. A conductive layer is a foil sheet of material having a relatively continuous electrical conductivity. Conductive layers preferably contain a metallic material, such as aluminum, to assist in detection from non-destructive inspection tests, such as eddy-current inspection. Aluminum is a relatively inexpensive material. The electrical conductivity of the conductive layer may vary depending on the required inspection intervals during a part lay-up process. The thickness of the conductive layer is configured to be sized so as to allow for detection at any level in the composite part by non-destructive inspection tests. For example, an aluminum foil when embedded half an inch deep inside a glass/epoxy composite laminate may need to be greater than or equal to 0.0005 inches in thickness to be detected by an eddy current inspection method. Although described as a foil sheet, a conductive layer is not so limited. Other forms or designs of material may be used.

Metallic materials, such as those used with the conductive layer tend to be susceptible to galvanic contamination when interacting with other electrically conductive materials. For example, material 107 may be a carbon fiber reinforced composite material of which the fiber is a conductor. In order to prevent galvanic contamination, an insulative layer is used to separate material 107 from the conductive layer. The insulative layer is configured to act as an electrical insulator and exhibit a relatively high dielectric property. An insulator can be natural and synthetic materials of any form 97 including, but not limited to, random fiber such as paper; woven fabric such as cloth; and paper or plastic sheets reinforced with unidirectional fiber strands or with woven fabric. Paper is relatively inexpensive as a material which makes it a cost effective selection. Although an insulative layer has been described as separating a conductive layer from material 107, where material 107 is composed of a material, such as glass, where galvanic contamination is not of concern, the conductive layer may contact material 107.

The insulative layer also permits the multi-function liner to be detectable through ultrasound, as opposed to eddy-current inspection as seen with conductive layers. An ultrasound inspection test is a common method for inspecting for embedded defects such as voids and wrinkles in cured composite parts. Insulative layers are configured to have a contrasting density to that of the density of material 107 and conductive layers. For example, material 107 and conductive layers may have a higher density than the insulative layer. Likewise, material 107 may be more or less dense than the conductive layers. By having a contrasting density to both the conductive layer and material 107, the insulative material, and the multi-function liner as a whole, may be detected using an ultrasound test. Features, such as the paper weight, surface finish and coating, and porosity, of an insulative layer are tailored to achieve a desired release property and to maximize the ability of the multi-function liner 101 to reflect sound when embedded within a cured part.

By configuring the insulative layer to have a contrasting density to that of the conductive layer, ultrasound and radiograph tests may also be used to detect residual portions of the multi-function liner of the present application. Although described as a paper based material, an insulative layer is not limited to paper or other forms 97 of materials. Any other insulative material that falls within the scope and intent of the present application may be used.

The multi-function liner is also configured to maintain a maximum thermal stability so that the multi-function liner maintains a desired shape when exposed to a variety of temperature ranges. This ability can be seen with the type of adhesive used to bond layers 91, 93 as described previously. Other ways to maintain thermal stability is in the selection of the materials used in layers 93.

The table of FIG. 2 illustrates selected embodiments 95 of the multi-function liner of the present application. Each of the embodiments 95 of the multi-function liner are illustrated with an "x" designating the layers 91, 93 included within the embodiment 95. Although only seven layers 91 are shown, it is understood that the multi-function liner may include more than seven layers 91.

Figure 3:
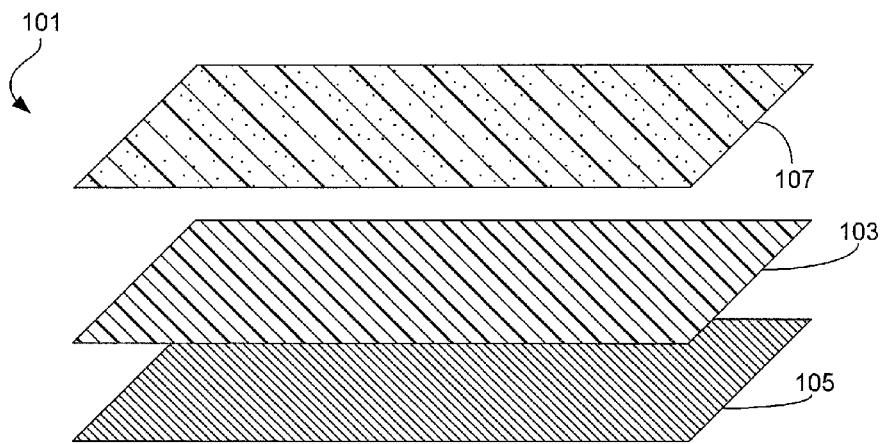
FIG. 3 is an isometric view of one embodiment of the multi-function paper liner as noted in FIG. 2, having a single insulative layer and a single conductive layer.
Figure 4:
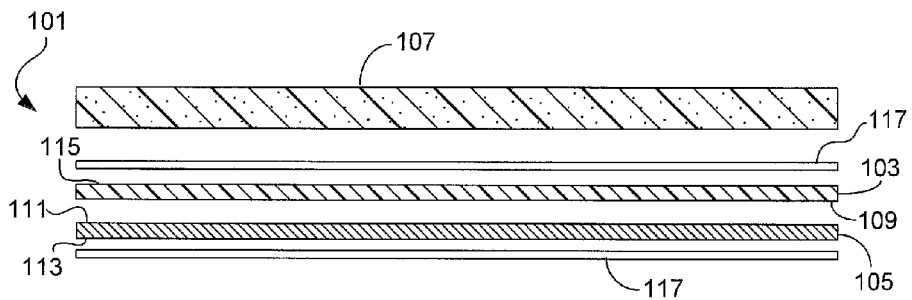
FIG. 4 is a side view of the multi-function paper liner of FIG. 3.

Referring now also to FIGS. 3 and 4 in the drawings, liner 101 is illustrated as an embodiment of the multi-function liner of the present application. A lower surface 109 of insulative layer 103 is configured to bond to an upper surface 111 of conductive layer 105 as described above. By bonding insulative layer 103 to conductive layer 105, the strength of liner 101 as a whole is stronger than the individual layers 103, 105. The bonding of insulative layer 103 to conductive layer 105 provides strength to liner 101. The minimum thicknesses of conductive layer 105 that is required for detection by non-destructive inspection tests depend on the sensitivities of the equipment used to perform the test. Alone, conductive layer 105 is susceptible to tearing. However, the combination of layers 103 and 105 serve to strengthen liner 101 to prevent tearing. Furthermore, the thickness of conductive layer 105 can be optimized to a minimum thickness for detection by non-destructive inspections tests when bonded to insulative layer 103 for increased strength. This allows liner 101 to save material and reduce costs.

Liner 101 is configured to engage and couple to one or more surfaces of material 107. Since liner 101 has a single insulative layer 103, liner 101 is oriented so as to allow an upper surface 115 of insulative layer 103 to contact material 107 in order to prevent galvanic contamination. However, due to liner 101 having a single insulative layer 103, when liner 101 is used, liner 101 is applied to both sides of material 107 to more easily permit transportation of the material 107 and liner 101 assembly, such as with rolled or flat sheets.

As seen in FIG. 4, a silicone layer 117 may be applied to surface 115 prior to contacting material 107. Furthermore, a second silicone layer 117 may be applied to a lower surface 113 of conductive layer 105. The use of silicone layers 117 is to provide a proper release function of liner 101 from material 107. Some embodiments may use a single silicone layer 117 to perform a proper release function and optionally apply an outer silicone layer 117. By not applying an optional outer silicone layer 117, a user can more easily identify and mark individual sheets or pieces of material 107. For example, a user can write or print on liner 101. Additionally, labels may be applied to, and removed from, liner 101 without causing damage to material 107, insulative layer 103, or conductive layer 105. Liner 101 includes one or more silicone layers 117.

Figure 5:
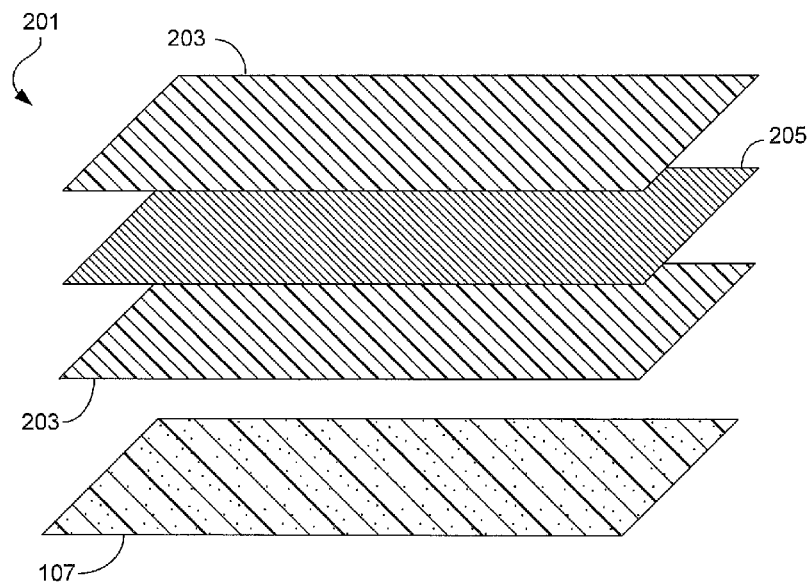
FIG. 5 is an isometric view of another embodiment of the multi-function paper liner as noted in FIG. 2 with two insulative layers and a conductive layer.
Figure 6:
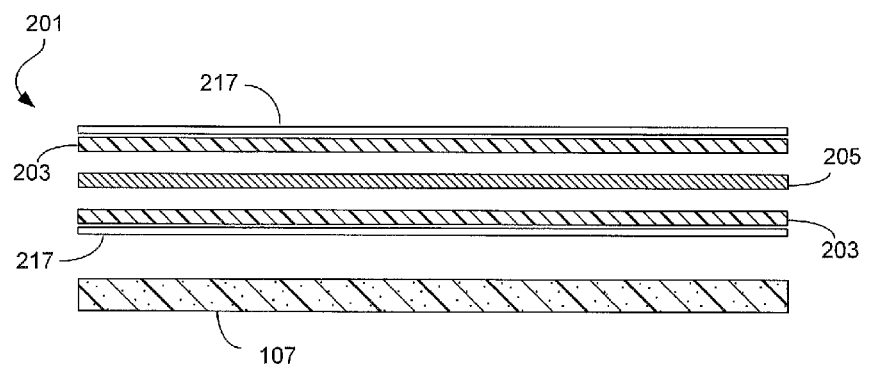
FIG. 6 is a side view of the multi-function paper liner of FIG. 5.

Referring now also to FIGS. 5 and 6 in the drawings, liner 201 is illustrated as another embodiment of the multi-function liner of the present application. Liner 201 is substantially similar in form and function to that of liner 101. All the features and characteristics associated with liner 101 are incorporated with respect to liner 201 except as noted herein. Liner 201 includes two insulative layers 203, an conductive layer 205, and an optional outer silicone layer 217. The term "outer" refers to the surface of the liner furthest from material 107 prior to rolling or stacking the composite assembly.

Liner 201 further includes a second insulative layer 203 similar to that of insulative layer 103. Insulative layer 203 has the same features and functions of insulative layer 103. Insulative layers 203 are configured to be bonded to opposing surfaces of conductive layer 205. The adhesive used is similar to that of the adhesive used in liner 101. Insulative layers 203 are configured to be coupled to a surface of material 107. As with liner 101, liner 201 may optionally include an outer silicone layer 217.

The inclusion of two insulative layers 203 reduces the risk of galvanic contamination. Furthermore, the use of liner 201 having two insulative layers 203, permits the use of a single liner to be used with material 107 when rolled or stacked. In this respect, both outer surfaces of liner 201 may contact material 107 without concern for galvanic contamination. Therefore, liner 201 allows for use of a single liner 201 and for the material 107 and liner 201 assembly to be rolled or layered for transportation and/or storage.

The addition of a second insulative layer 203 also serves to further strengthen liner 201. Additionally, liner 201 is able to further optimize the size, features, and characteristics of the individual layers 203 and 205 to reduce costs, optimize resources, and increase performance and detection.

Referring now also to FIGS. 7-12 in the drawings, liners 301, 401, 501, 601, 701, and 801 are illustrated as other embodiments of the multi-function liner of the present application. The form and function of the conductive layers, insulative layers, and silicone layers are similar to that as described with respect to FIGS. 3-6.

Figure 7:
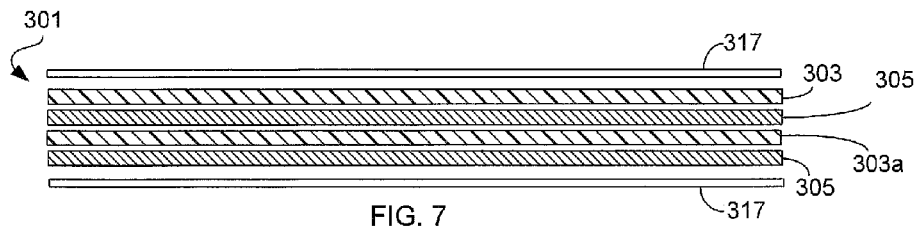
FIG. 7 is a side view of another embodiment of the multi-function paper liner as noted in FIG. 2, having two insulative layers and two conductive layers.

With respect to FIG. 7, two conductive layers 305 and two insulative layers 303 are used with a liner 301. As noted previously, the layers 303, 303*a*, and 305 are alternated, so that neighboring layers are not of the same type. The limitations of liner 101 as pertaining to needing to use two liners with material 107 apply equally here with liner 301 due to an outer most layer being a conductive layer 305. At least one silicone layer 317 is used.

Figure 8:
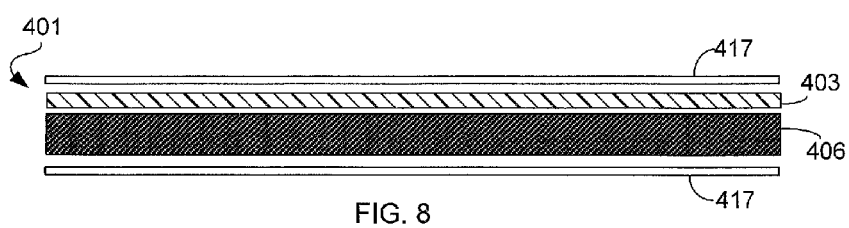
FIG. 8 is a side view of another embodiment of the multi-function paper liner as noted in FIG. 2, having an integrated layer and a single insulative layer.

In particular to FIG. 8, liner 401 uses a single insulative layer 403 and an integrated layer 406. Insulative layer 403 and integrated layer 406 are bonded together along a surface similar to that of layers 103 and 105 of liner 101. Integrated layer 406 is a combination of different materials that form a hybrid material. An example of such hybrid materials are metal vapor coated paper, metal vapor coated fiber strands, or fabric. Integrated layer 406 is configured to replace and/or be a combination of one insulative layer and two conductive layers. It is understood that other embodiments of integrated layer 406 may included more or less insulated and/or conductive layers (see FIGS. 10-12).

Depending on the conductivity characteristics of integrated layer 406, the same limitations as seen with liner 101 concerning the orientation of the liner and the number of liners needed to be used with material 107 may apply. Concerns regarding galvanic contamination may be a factor used to determine which layers 403, 406 may contact material 107 and the number of liners 401 used with material 107. At least one silicone layer 417 is used.

Figure 9:
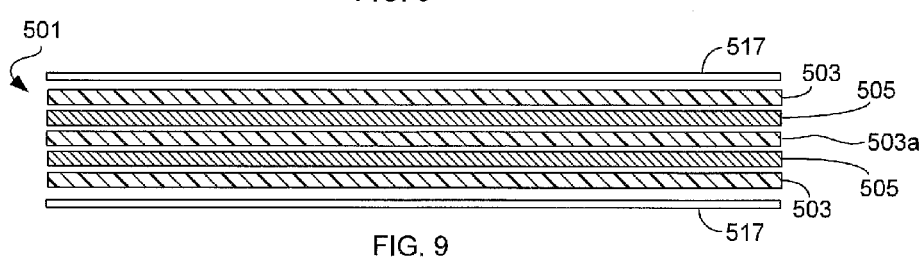
FIG. 9 is a side view of another embodiment of the multi-function paper liner as noted in FIG. 2, having three insulative layers and two conductive layers.

In particular to FIG. 9, liner 501 includes three insulative layers 503, 503*a* and two conductive layers 505 along with at least one silicone layer 517. As noted previously, the layers 503, 503*a*, and 505 are alternated, so that neighboring layers are not of the same type. The limitations of liner 201 as pertaining to the orientation of and the number of liners used with material 107 apply equally here with liner 501 due to an outer most layer being an insulative layer 505.

An additional benefit of liner 501 is the sandwiching effect of conductive layers 505 on opposing surfaces of insulative layer 503*a*. During the process of applying the multi-function liner to material 107, a resin can be applied to a multi-function liner and transferred to the dry fibrous material through a heating process. In so doing, the resin can seep into the pores of the insulative layer and alter the density of that layer thereby making it more difficult to detect through non-destructive inspection tests. This seepage of resin into an insulative layer applies limitations on the characteristics of the insulative layer exposed to the resin. Options concerning choices such as porosity, surface finish, and coating may be limited to avoid resin seepage. However, insulative layer 503*a*, located between conductive layers 505, is protected from resin seepage because conductive layers 505 act as a shield. This allows for the sandwiched insulative layer 503*a* to have different properties from the outer most insulative layers 503 and ultimately allow liner 501 to become more detectable to non-destructive inspection tests. This same advantage is applicable to any insulative layer located between two conductive layers. Alternate embodiments may be configured to have insulative layers 503 and 503*a* made of different types of material. For example, insulative layer 503 may be a paper and insulative layer 503*a* a cloth for added porosity and increased physical rupture and tear strength. Liner 301 in FIG. 7 also exhibits this characteristic as seen with layer 303*a*.

Figure 10:
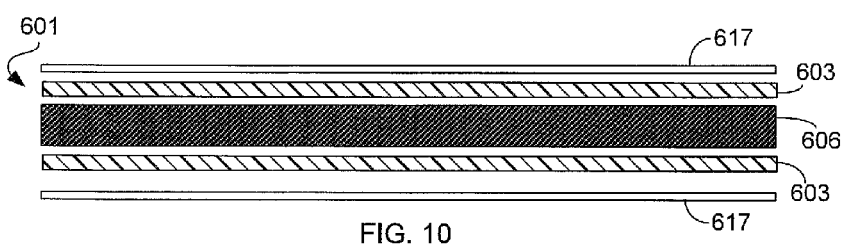
FIG. 10 is a side view of another embodiment of the multi-function paper liner as noted in FIG. 2, having two insulative layers and an integrated layer.

In particular to FIG. 10, liner 601 includes two insulative layers 603 bonded to opposing surfaces of an integrated layer 606. At least one silicone layer 617 is used. Integrated layer 606 is similar in form and function to that of integrated layer 406 in FIG. 8.

Figure 11:
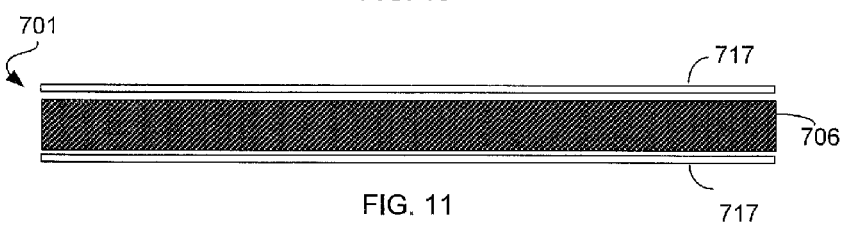
FIG. 11 is an isometric view of another embodiment of the multi-function paper liner as noted in FIG. 2, having a single integrated layer and two silicone layers.

In particular to FIG. 11, liner 701 includes an integrated layer 706 and at least one silicone layer 717. Integrated layer 706 is similar in form and function to that of layer 406 and 606 above. However, integrated layer 706 is configured to replace and/or be a combination of three insulative layers and two conductive layers.

Although a multi-function liner has been described as having a conductive layer and an insulative layer, liner 701 illustrates an embodiment wherein the characteristics and features of both an insulative layer and a conductive layer are integrated into a single layer. In such situations, one layer, integrated layer 706, may be used and yet still allow for detection of the multi-function liner through a plurality of non-destruction inspection methods.

Figure 12:
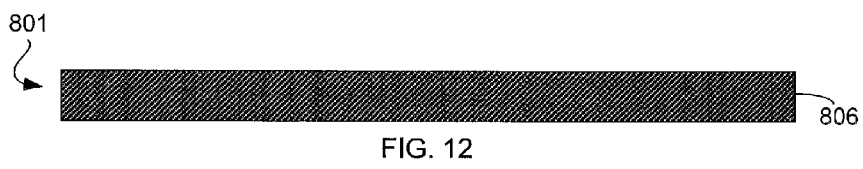
FIG. 12 is a side view of another embodiment of the multi-function paper liner as noted in FIG. 2, having a single integrated layer.

In particular to FIG. 12, liner 801 includes an integrated layer 806. Integrated layer 806 is similar in form and function to that of layer 706 above. However, liner 801 differs from liner 701 in that silicone layers are not needed because the release function is provided intrinsically by the integrated layer 806.

It is understood that any of the preceding insulative layers described within FIGS. 3-12 can include metallic coating deposited on the layers and conductive fillers mixed within the layers. Conductive fillers may include metallic strings, shavings, flakes, wire mesh or metal coated organic fibers to name a few. In such an embodiment, an insulative layer, when consisting of a sufficiently large amount of metallic content, can replace a conductive layer because it becomes conductive enough to be detected by an eddy current inspection test, for example. However, other embodiments may include both types of conductive layers within a liner.

Furthermore, although the preceding conductive layers within FIGS. 3-12 have been described as a sheet having a relatively uniform thickness, it is understood that conductive layers may also include a plurality of continuous strings lined in a parallel pattern along an edge of an insulative layer. It is preferred that the strings be spaced relatively equally. The distance between strings may be selected to adjust the density, strength, and detectability of the liner. It is preferred that conductive layers be oriented so as to run the strings along the length of material 107, so as to be predominantly in tension if possible.

The conductive layer may also be a wire mesh bonded to a surface of an insulative layer. The spacing of the grid for conductive layer may be selected to adjust the density, strength, and detectability of the liner to non-destructive inspection tests. Additionally, conductive layers described within this specification are not limited to these specific embodiments described.

Figure 13:
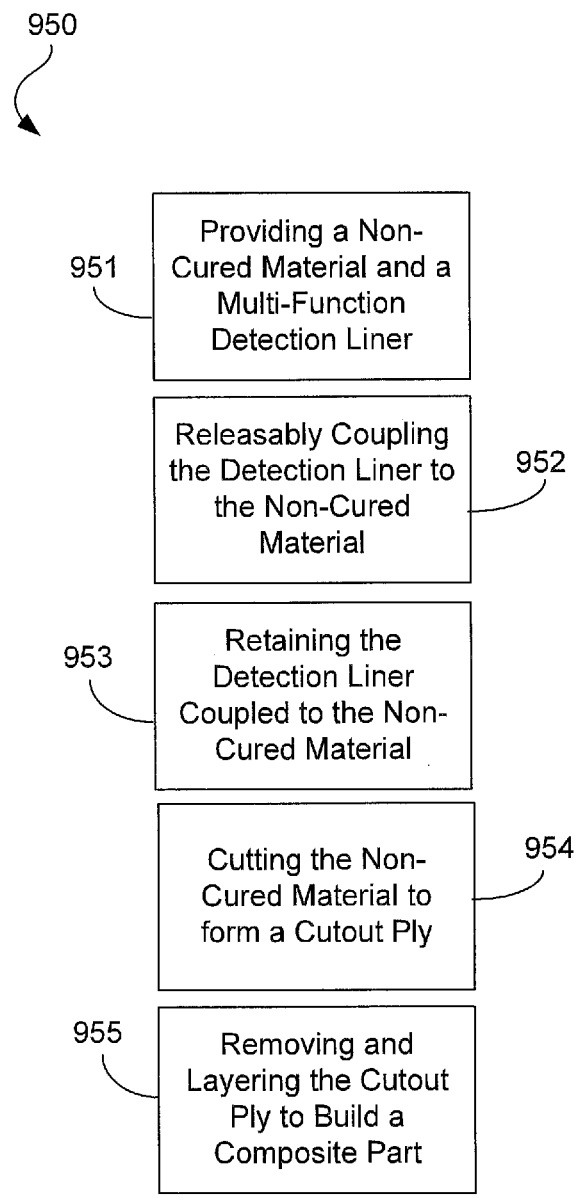
FIG. 13 is a chart of the preferred method of manufacturing a composite material according to the preferred embodiment of the present application for use in forming a composite part through a part lay-up process.

Referring now also to FIG. 13 in the drawings, a chart 950 of the method of manufacturing a composite part is illustrated. A prepreg material and a multi-function liner are provided 951. The multi-function liner has insulative and conductive properties found within one or more layers sufficient to make the multi-function liner detectable to a plurality of non-destructive inspection tests. The liner is releasably coupled 952 to the prepreg material to form a multi-function composite material assembly. Combining of the multi-function liner and prepreg material occurs during manufacturing of the prepreg material. Prior to coupling the prepreg material and the multi-function liner together, the thicknesses and types of the layers are selectively sized and configured to permit detection of the liner at any level within the composite part through the plurality of non-destructive inspection tests. For example, the layers may be configured as described previously in FIGS. 3-12.

The liner is retained 953 on the prepreg material from manufacturing, transportation, cutting, and preparation of the material until the prepreg is layered. Prior to layering, the sheet of prepreg and the liner are cut 954 to generate a composite cutout ply having a selectively shaped pattern. The cutout ply is layered 955 to build a laminated composite part formed from a plurality of composite cutouts plies. The liner is removed from the cutout ply prior to layering. A non-destructive inspection test is performed on the composite part during and after lay-up to detect any residue portions of the liner remaining between the layers.

The current application has many advantages over the prior art including the following: (1) reduced cost of manufacturing a composite part by not having to replace the liner; (2) a liner that is releasably bonded to the composite material and is detectable through a plurality of non-destructive inspection tests; (3) prevent galvanic contamination; (4) a stronger liner that is less susceptible to tearing when handled; and (5) a liner that is applied at the point of manufacturing of the prepreg material and provides proper liner functions throughout the lay-up process.

The particular embodiments disclosed above are illustrative only, as the application may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. It is apparent that an application with significant advantages has been described and illustrated. Although the present application is shown in a limited number of forms, it is not limited to just these forms, but is amenable to various changes and modifications without departing from the spirit thereof.

What is claimed is:

1. A multi-function composite material assembly for use in the lay-up of a composite part, the composite material assembly comprising:
   a non-cured composite material; and
   a multi-function detection liner comprising:
   a first insulative layer having a density in contrast to that of the non-cured composite material, such that the first insulative layer is detectable by ultrasound within the composite part;
   a first conductive layer bonded to the first insulative layer and configured to provide an eddy current signal and to enhance ultrasound attenuation of the detection liner within the composite part, the first conductive layer including a first conductive mesh; and
   a second conductive layer bonded to the first insulative layer and the first conductive layer, the second conductive layer including a second conductive mesh,
   wherein the detection liner is releasable from a surface of the non-cured composite material during the lay-up process.

2. The multi-function composite material assembly of claim 1, wherein the first insulative layer and the first conductive layer are configured to be detected by a plurality non-destructive inspection methods.

3. The multi-function composite material assembly of claim 1, wherein the first insulative layer is applied to the surface of the non-cured composite material.

4. The multi-function composite material assembly of claim 1, further comprising:
   a second insulative layer bonded to a lower surface of the first conductive layer opposite the first insulative layer, the second insulative layer configured to have a density varied from that of the non-cured composite material and the composite part.

5. The multi-function composite material assembly of claim 4,
   wherein the second conductive layer is configured to provide additional strength.

6. The multi-function composite material assembly of claim 5, wherein the layers are alternated within the detection liner are alternated between insulative layers and conductive layers.

7. The multi-function composite material assembly of claim 5, wherein the first conductive layer and the second conductive layer are bonded to opposing surfaces of the second insulative layer.

8. The multi-function composite material assembly of claim 7, wherein the features of the second insulative layer is different from the features of the first insulative layer, so as to increase detection through non-destructive inspection tests.

9. The multi-function composite material assembly of claim 1, further comprising:
   an integrated layer having properties and features of a conductive layer and an insulative layer.

10. The multi-function composite material assembly of claim 1, wherein the first insulative layer includes conductive fillers such as a metallic fiber and a metal coated non-conductive fiber.

11. The multi-function composite material assembly of claim 1, wherein the detection liner is capable of withstanding elevated temperatures above 200 degrees Fahrenheit.

* * * * *